United States Patent [19]
Hori et al.

[11] Patent Number: 5,156,823
[45] Date of Patent: Oct. 20, 1992

[54] DEVICE FOR AND METHOD OF TREATING WASTE LIQUID

[75] Inventors: Shoji Hori, Nara; Koichi Tokuhisa, Fukuoka, both of Japan

[73] Assignee: Daiken Iki Co., Ltd., Japan

[21] Appl. No.: 445,768

[22] Filed: Dec. 4, 1989

[30] Foreign Application Priority Data

Dec. 6, 1988 [JP] Japan .................................. 63-309669
Apr. 17, 1989 [JP] Japan .................................. 1-44582[U]

[51] Int. Cl.$^5$ ................................................ A61L 2/00
[52] U.S. Cl. ...................................... 422/292; 422/102;
422/103; 422/104; 422/256; 210/198.1;
210/206; 141/363
[58] Field of Search ................. 422/292, 295, 73, 102,
422/103, 104, 256; 210/198.1, 206, 207;
222/129.2; 141/363, 364, 365, 366; 4/222-232

[56] References Cited

U.S. PATENT DOCUMENTS

| | | | |
|---|---|---|---|
| 3,061,842 | 11/1962 | Woodruff | 141/363 |
| 3,736,101 | 5/1973 | Pirtle, Jr. | 422/256 |
| 4,358,860 | 11/1982 | Church | 4/228 |
| 4,790,981 | 12/1988 | Mayer et al. | 422/266 X |

Primary Examiner—Robert J. Warden
Assistant Examiner—Laura E. Collins
Attorney, Agent, or Firm—Sixbey, Friedman, Leedom & Ferguson

[57] ABSTRACT

A waste liquid treating device is provided above a waste container or in the upper portion thereof with a container, suspender or the like for holding a waste liquid treating chemical agent. The chemical agent is preferably a coagulant for the waste liquid to be treated or an agent for killing bacteria, viruses or the like present in the liquid. A waste liquid treating method is practiced using the device. The waste liquid collected in the waste container is treated with the chemical agent held above or in the upper portion of the waste container and thereafter discarded along with the waste container.

16 Claims, 6 Drawing Sheets

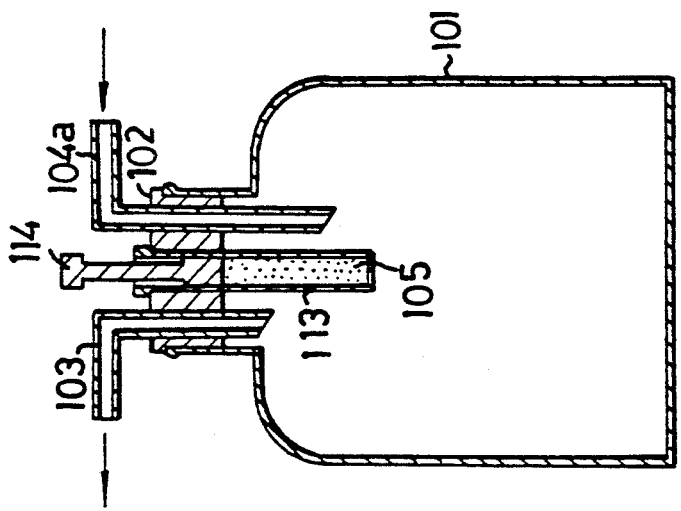
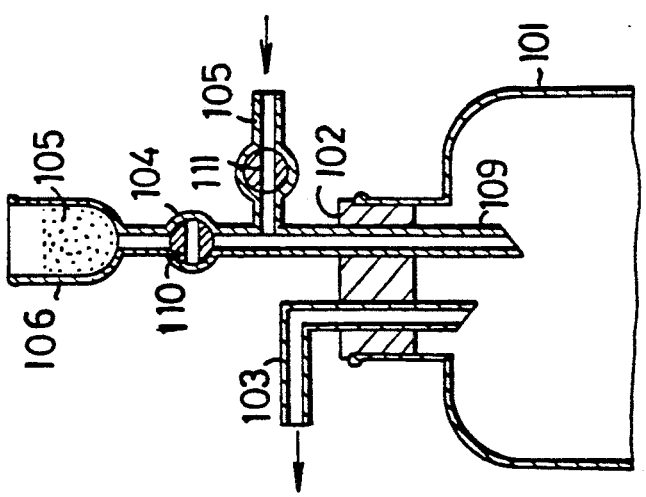
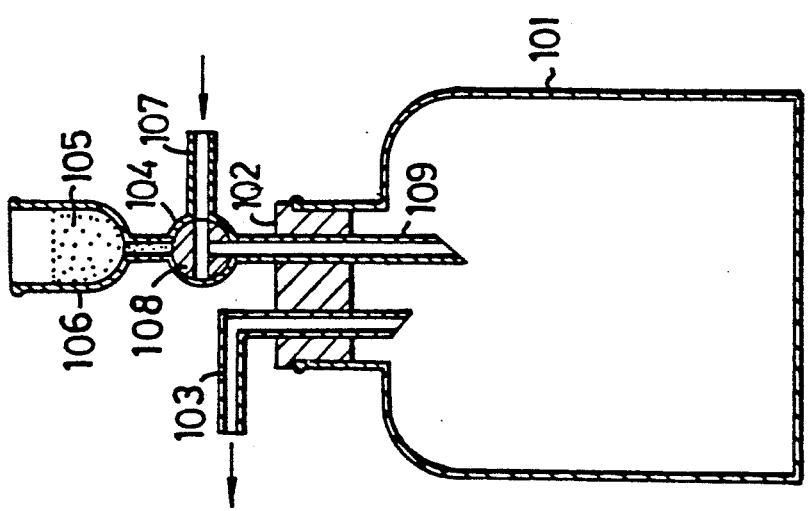

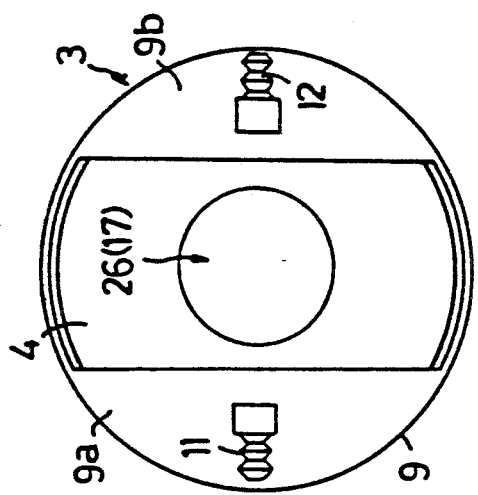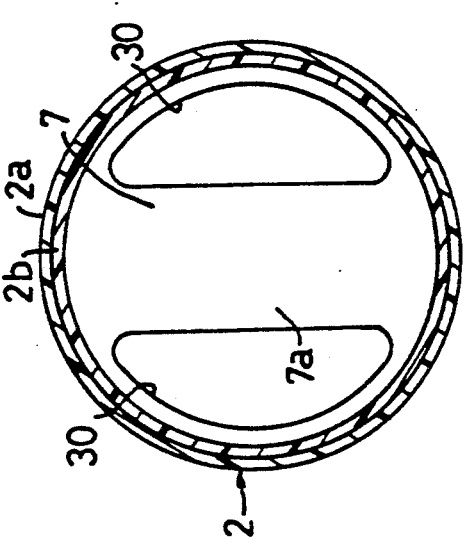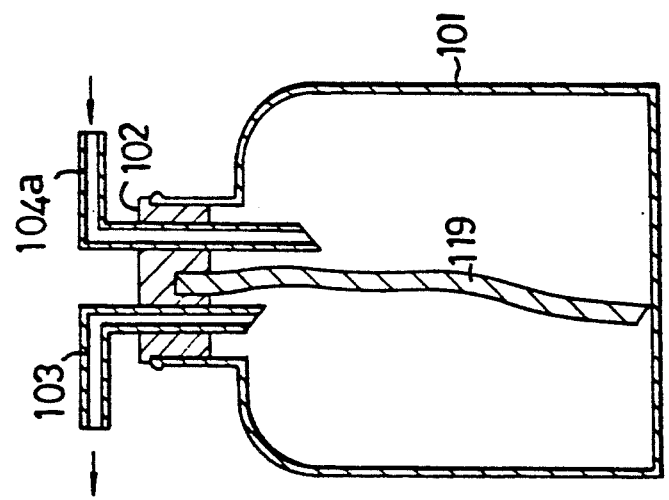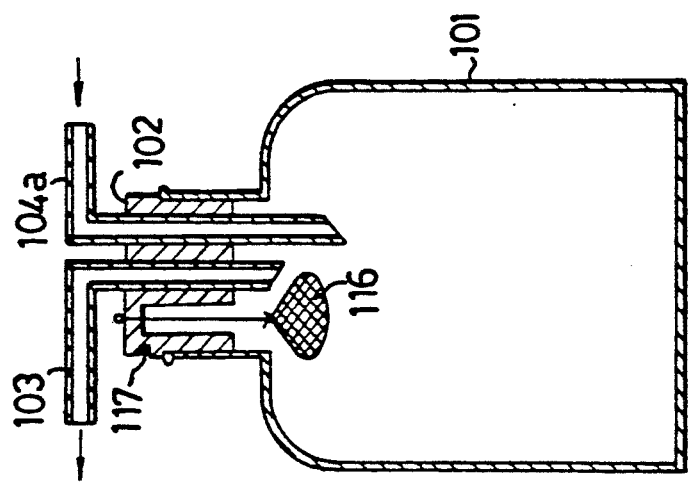

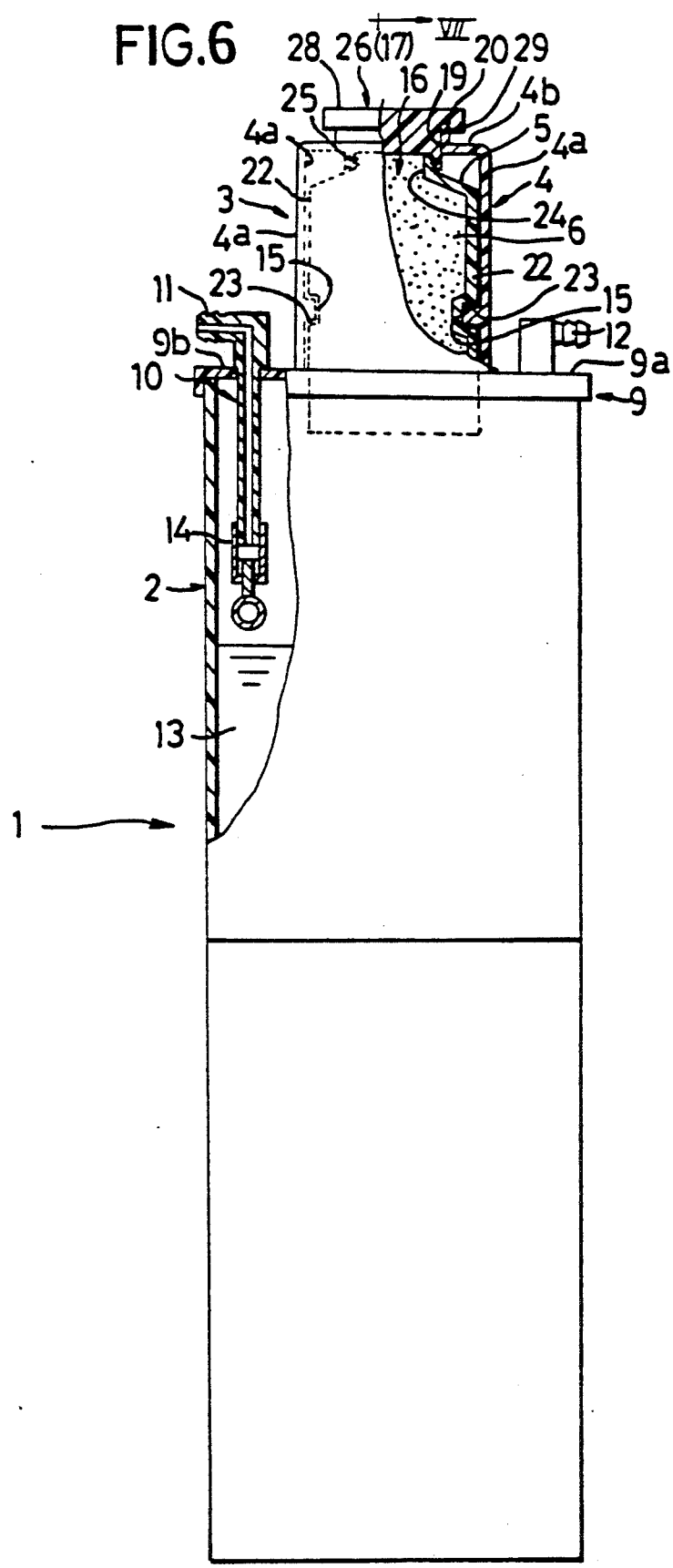

DEVICE FOR AND METHOD OF TREATING WASTE LIQUID

FIELD OF THE INVENTION AND RELATED ART STATEMENT

The present invention relates to devices for and methods of treating waste liquids harmful to the human body.

Examples of such waste liquids are the blood, lymph and pus released from patients during surgery, saline washings from the affected part, etc.

These waste liquids are very likely to contain harmful bacteria, viruses or the like and are also likely to cause infections with such bacteria, viruses or the like when the living body is exposed to the waste liquid. Accordingly, such a body fluid or the waste liquid containing the body fluid is usually collected from the body cavity into a waste container.

The waste liquid collected in the container is transported to a treating facility, sterilized as accommodated in the container with steam or the like, and discarded as a waste. The waste container emptied of the waste liquid is washed, sterilized and used again.

However, the waste container, when made of glass, is fragile and difficult to handle because it is heavy. Accordingly, if the container is inadvertently dropped during transport from the operating room to the sterilizing facility, the container breaks to spill or scatter the unsterilized waste liquid, hence a great hazard. Further when the waste liquid is discharged into a storage container at the waste treating facility, the worker handling the waste is exposed to the hazard of infection.

Unexamined Japanese Patent Publication SHO 51-48589 discloses a waste liquid container of synthetic resin which is disposable without being reused again. The waste container thus made of synthetic resin is lighter and easier to handle than the glass container. Furthermore, the disposable container can be incinerated along with the waste liquid at the treating facility.

Nevertheless, the synthetic resin waste container is still likely to break and leak or spill the waste liquid at the treating facility or during transport thereto. Such disposable waste containers which are easy to handle are not infrequently disposed of by the hand of an agent other than the hospital. The container will then be transported for a longer period of time and becomes more likely to break, possibly causing a hazard to persons outside the hospital.

OBJECT AND SUMMARY OF THE INVENTION

In view of the above situation, the main object of the present invention is to avoid the foregoing hazards by providing a device for and a method of treating a waste liquid with a chemical agent immediately after the liquid has been collected in a waste container.

The present invention provides a waste liquid treating device comprising means for holding a chemical agent for treating a waste liquid, the holding means being provided above or in the upper portion of a waste container. With use of this device, the waste liquid collected in the container can be immediately treated with the chemical agent held by the holding means, whereby the possible hazard to the human body is avoidable even if the waste container breaks thereafter.

When the chemical agent holding means is made removably attachable to the waste container, the holding means can be attached to the container after the waste liquid has been collected in the container. A glass bottle or the like, which is widely used as a waste liquid container, is then readily usable for the present device. Furthermore, one of the chemical agent holding means and the waste container is then conveniently reusable.

The chemical agent holding means may be made inseparable from the waste container as a unit.

When the waste liquid treating chemical agent is one for coagulating the waste liquid, the waste liquid becomes nonflowable and therefore will not leak or spill even if the container breaks.

Various high-molecular-weight water-absorbing polymers are chiefly usable as coagulants. Examples of useful polymers are sodium polyacrylate, starch-acrylic acid graft polymer, saponified product of vinyl acetate-methyl acrylate copolymer, saponified product of vinyl acetate-maleic anhydride copolymer and saponified product of isobutylene-maleic anhydride. These high-molecular-weight water-absorbing polymers can be used in combination with pulp and like organic materials, silica and like inorganic materials and, when desired, disinfectants, bactericides, fungicides and the like, as suitably admixed therewith. Although the coagulant is used generally in the form of a powder or granules, a nonwoven fabric impregnated with the coagulant, or the coagulant sandwiched between pieces of such fabric can be used as cut to a strip or any desired shape, depending on the method of application. The coagulant may be used in the form of a liquid.

When the waste liquid treating chemical agent is adapted to kill the bacterium or virus in the waste liquid or make such a microorganism less infectant, the waste liquid can be made harmless to the human body. In this case, it is desirable to use a coagulant in combination with the agent.

When the waste liquid is made to be aspirated into the waste container by giving a negative internal pressure to the container, the device is convenient to use for collecting the blood, lymph or like waste liquid from the patient during surgery at the hospital.

The waste container may be provided at a vertically intermediate portion thereof with a baffle plate for impeding the settlement of the treating chemical agent. The chemical agent will then partly remain on the baffle plate, acting to treat the waste liquid in the vicinity thereof. This shortens the time required for the treatment of the waste liquid.

Preferably, the chemical agent holding means comprises a container for accommodating the treating chemical agent, and the chemical agent container is adapted to communicate with the waste container through a shutoff value. The waste container, when given a negative internal pressure in this case, aspirates the waste liquid thereinto, and the shutoff value serves also as a shutoff value for the waste liquid inlet port. The shutoff valve holds the inlet port closed while holding the chemical agent container in communication with the waste container. The valve holds the inlet port open while holding the chemical agent container out of communication with the waste container.

Preferably, the chemical agent container is so held as to fall inside the waste container and is adapted to pass aqueous solutions therethrough. When the chemical agent container is caused to fall into the waste liquid within the waste container, the treating chemical agent diffuses through the agent container into the waste liquid.

Preferably, the chemical agent container so held as to fall inside the waste container is made soluble in water. When allowed to fall into the waste liquid in this case, the chemical agent container dissolves, permitting the agent to diffuse through the waste liquid.

Preferably, the chemical agent holding means comprises a suspender for holding the waste liquid treating chemical agent, and the suspender is held suspended within the waste container and is adapted to pass aqueous solutions therethrough. When the waste liquid is collected in the waste container in this case, the chemical agent container is immersed in the waste liquid, permitting the agent to diffuse through the container into the waste liquid.

Preferably, the chemical agent container has a chemical agent delivery opening and is so supported as to make the delivery opening changeable selectively to an upwardly directed position or to a downwardly directed position. When the waste liquid is collected in the waste container and the chemical agent container is thereafter moved to bring the delivery opening to the downwardly directed position, the chemical agent is placed into the waste liquid. Preferably, the chemical agent container is rotatably supported. It is convenient that the center of rotation of the chemical agent container be at a position away from the center of gravity thereof so that the delivery opening is in the downwardly directed position when the chemical agent container is in a stable state, and that means be provided for releasably holding this container in the position in which the delivery opening is directed upward. When the chemical agent container is released from this position after the waste liquid has been collected in the waste container in this case, the chemical agent container rotates under gravity to direct the delivery opening downward and place the chemical agent into the waste liquid. The means for releasably holding the agent container in the position wherein the delivery opening is directed upward may serve also as means for openably closing the delivery opening. The waste treating chemical agent can then be prevented from degradation or spillage.

The chemical agent container can be made releasable from outside the waste container to change the delivery opening from the upwardly directed position to the downwardly directed position. The agent container is then easily so releasable with high safety. Preferably in this case, the chemical agent holding means comprises a hollow closure for closing an upper opening of the waste container, the hollow closure being formed with a release opening located above the delivery opening as directed upward, the release opening being closed with a stopper for closing the delivery opening. Further preferably, the stopper is in screw-thread engagement with respective threaded portions of the delivery opening and the release opening, and the threaded portions are in opposite-handed screw relationship with each other, the chemical agent container being so supported as to be movable upward or downward relative to the hollow closure.

The device of the present invention is suitable for practicing a method of treating a waste liquid characterized by treating the waste liquid as collected in a waste container with a chemical agent held above or in the upper portion of the waste container, and discarding the treated waste liquid along with the waste container. With this method, the chemical agent may be placed into the waste liquid after the liquid has been collected in the container, or may be held by a suspender permeable to an aqueous solution and held suspended inside the waste container before the waste liquid is collected in the waste container. Further with this method, the waste liquid may be aspirated into the waste container by giving a negative internal pressure to the waste container. The method thus adapted is especially suited to the treatment of the blood or the like released from the patient during surgery. In this case, the waste container is prepared from synthetic resin and thereby made resistant to breakage. Further when a coagulant for the waste liquid is used as the chemical agent, the waste liquid will not leak or spill even if the waste container breaks.

BRIEF DESCRIPTION OF THE DRAWINGS

FIG. 1 is a sectional view showing a waste liquid treating device as a first embodiment of the invention;

FIG. 2 is a sectional view showing another waste liquid treating device as a second embodiment;

FIG. 3 is a sectional view showing another waste liquid treating device as a third embodiment;

FIG. 4 is a sectional view showing another waste liquid treating device as a fourth embodiment;

FIG. 5 is a sectional view showing another waste liquid treating device as a fifth embodiment;

FIG. 6 is a side elevation partly broken away and showing another waste liquid treating device as a sixth embodiment;

FIG. 8 is a plan view of the device shown in FIG. 6;

FIG. 9 is a view in section taken along the line IX—IX in FIG. 7; and

DESCRIPTION OF THE PREFERRED EMBODIMENTS

Figure 7:
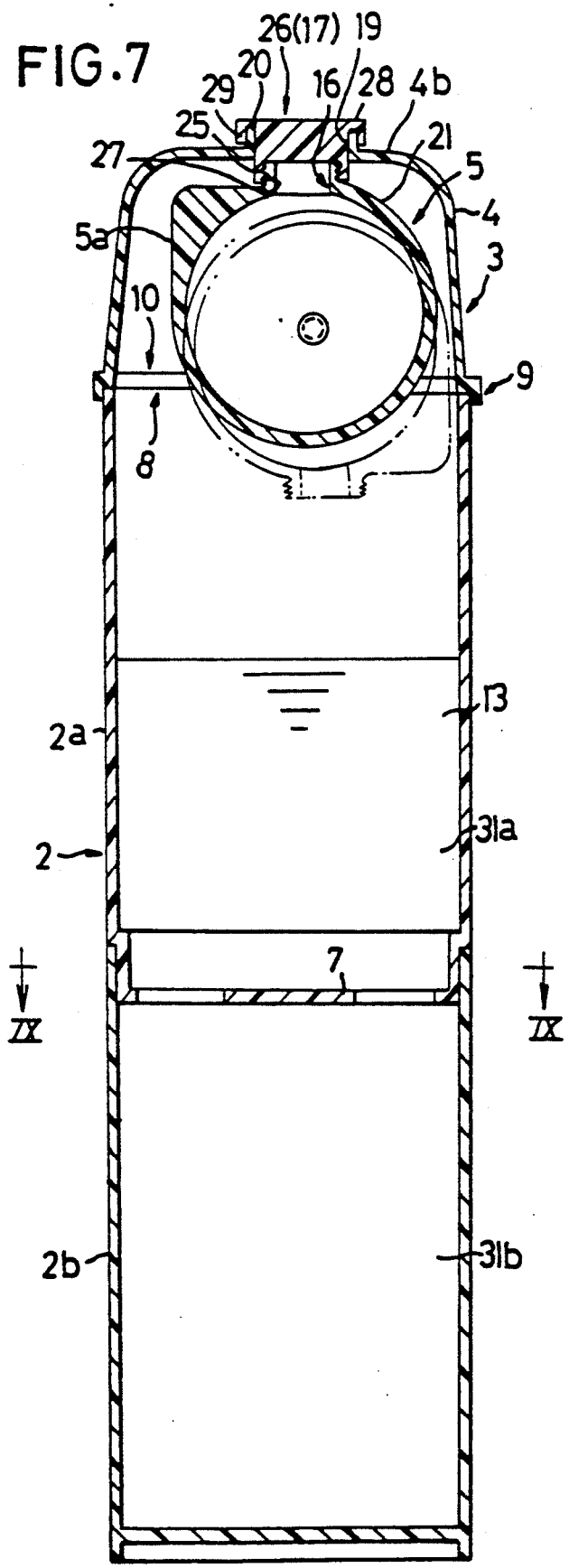
FIG. 7 is a view in section taken along the line VII—VII in FIG. 6.

FIG. 1 shows a first embodiment, i.e. a device for treating a waste liquid. The device has means for holding a chemical agent for treating the waste liquid. The chemical agent holding means is disposed above a container 101 for collecting the waste liquid (waste container).

The waste container 101 is made of a transparent or semitransparent synthetic resin and can be prepared from a suitable material in a suitable shape.

The waste container 101 has an opening which is fitted with a stopper 102 made of a flexible material such as soft synthetic resin or rubber. An L-shaped air discharge pipe 103 and a waste liquid inlet pipe 104 extend through and are attached to the stopper 102. The liquid inlet pipe 104 has a lower pipe portion 109 and is formed at its upper portion with a branch pipe portion 107 and a chemical agent container (chemical container) 106 for accommodating a coagulant 105. The inlet pipe 104 is internally provided with a shutoff valve 108, through which the chemical container 106 or the branch pipe portion 107 communicates with the lower pipe portion 109 inserted into the container 101. More specifically, when the valve 108 is in the illustrated state, the branch pipe portion 107 communicates with the lower pipe portion 109. When the shutoff valve 108 is rotated clockwise, the chemical container 106 communicates with the lower pipe portion 109. The air discharge pipe 103 is connected to a vacuum pump, and the branch pipe portion 107 to the patient, each through a suitable tube. Thus, the shutoff valve 108 serves also as a shutoff valve for the liquid inlet port of the device.

To treat a waste liquid with the device described, air is discharged from inside the waste container 101 through the pipe 103 first to give a negative internal pressure to the waste container 101, whereupon the waste liquid released from the patient flows into the branch pipe portion 107 of the inlet pipe 104 through the tube and is collected in the container 101 by suction. At this time, the rotatable member of the valve 108 is of course so positioned that the branch pipe portion 107 communicates with the lower pipe portion 109.

On completion of collection of the waste liquid, the valve 108 is rotated to hold the chemical container 106 in communication with the lower pipe portion 109 to place the coagulant 105 in the chemical container 106 into the waste liquid. The liquid collected in the container 101 is promptly coagulated with the coagulant 105 and is thereafter discarded along with the container 101, the air discharge pipe 103 and the liquid inlet pipe 104.

Although the coagulant can be placed into the container 101 without negatively pressurizing the interior of the container 101, a negative pressure, if given, expedites the application of the coagulant.

The stopper 102, the air discharge pipe 103 and the liquid inlet pipe 104 may be molded integrally.

FIG. 2 shows another waste liquid treating device as a second embodiment, which has two shutoff valves 110 and 111 in place of the shutoff valve 108 of the first embodiment. The chemical container 106 is brought into and out of communication with the lower pipe portion 109 through the valve 110, and the branch pipe portion 107 is adapted to communicate with the lower pipe portion 109 through the other valve 110. With exception of this feature, the second embodiment has the same construction as the first; like parts are designated by like reference numerals throughout the drawings concerned.

In the case of the second embodiment, the valve 110 is closed and the other valve 111 is opened when a negative internal pressure is to be given to the waste container 101. The chemical agent is placed into the waste liquid by opening the valve 110 with the other valve 111 closed. In this case, the air discharge pipe 103 may be closed by an unillustrated shutoff valve after the valve 111 has been closed to maintain the container 101 at a negative internal pressure, followed by opening of the valve 110 for the application of the chemical agent.

FIG. 3 shows another waste liquid treating device as a third embodiment, wherein a chemical agent container 113 in the form of a short pipe having a closed bottom is attached to the stopper 102. A piston 114 is fitted in the container 113 from above. A coagulant is accommodated i the chemical container 113 under the lower end of the piston 114. When a waste liquid has been collected in the container 101, the piston 114 is depressed, whereupon the container 113 breaks and falls along with the coagulant 105 therein into the waste liquid collected in the container 101. The chemical container 113, which is made of synthetic resin, glass or the like, may locally have a thin wall portion so as to be readily breakable. Indicated at 104a is an L-shaped waste liquid inlet pipe. The air discharge pipe 103, the inlet pipe 104a and the chemical container 113 may be molded of synthetic resin integrally with the stopper 102.

FIG. 4 shows another waste liquid treating device as a fourth embodiment, in which a container 116 having a coagulant enclosed therein is suspended from a stopper 102 with a thread. The chemical container 116 is made of a fabric, nonwoven fabric, netting or the like which is permeable to aqueous solutions, or of a water-soluble film or the like. The stopper 102 is formed with a groove 117. When a waste liquid has been collected in the waste container 101, the stopper 102 is cut at the groove 117 to cut the thread suspending the chemical container 116 with a suitable cutter, whereupon the container 116 falls along with the coagulant to coagulate the waste liquid collected in the waste container 101. An air discharge pipe 103 and a waste liquid inlet pipe 104a are the same as those of the third embodiment.

FIG. 5 shows another waste liquid treating device, i.e. a fifth embodiment, wherein a suspender 119 is suspended from the stopper 102. The suspender 119 is made of a material, such as a nonwoven fabric, permeable to aqueous solutions, cut to the shape of a strip, string or the like and contains a coagulant. When a waste liquid is collected in the waste container 101 in which the suspender 119 is held suspended, the waste liquid is coagulated with the coagulant. The device has the same air discharge pipe 103 and liquid inlet pipe 104a as the third embodiment.

FIGS. 6 to 9 show another waste liquid treating device, i.e. a sixth embodiment, in which the present invention is applied to a disposable aspirator 1. The device is made entirely of a synthetic resin and comprises a waste container 2, a hollow closure 3 joined to the upper portion of the container 2, and a chemical agent container 5 rotatably supported by the closure 3 as disposed inside thereof. The closure 3 may be removable from the waste container 2 or inseparably integral therewith. According to the present embodiment, the chemical container 5 is filled with a powdery chemical agent 6 which comprises a mixture of bactericide for killing bacteria or the like present in the waste liquid and a coagulant for solidifying the liquid like agar.

The waste container 2 is in the form of a hollow cylinder having an open upper end. To provide the baffle plate 7 to be described later, the container 2 comprises two divided portions, i.e. upper and lower portions, which are welded together.

FIG. 7 is a view in section taken along the line VII—VII in FIG. 6, and FIG. 8 is a plan view of FIG. 6. As seen in these drawings, the closure 3 joined to the waste container 2 has a generally box-shaped hollow portion 4 having a rectangular bottom opening 8, and the peripheral edge of the hollow portion 4 defining the opening 8 is formed with a flange 9, by which the closure is joined to the upper open end 10 of the waste container 2 to close the open end 10.

With reference to FIGS. 6 and 8, the flange 9 comprises a pair of portions 9a, 9b each resembling a bow when seen from above and positioned on opposite sides of the hollow portion 4. The bowlike portion 9a at one side is provided with an outlet member 11 for connection to a suction source such as a suction pump, and the other bowlike portion 9b with an inlet member 12 to be connected to a tube for aspirating a waste liquid containing a body fluid. The waste container 2 in communication with the outlet of the member 11 is internally provided with a float valve 14 for automatically discontinuing aspiration when the container 2 is filled with the waste liquid 13.

The opposed side walls 4a, 4a of the hollow portion 4 are integrally formed on the inner side thereof with projecting pivots 15, 15, respectively, for rotatably supporting the chemical container 5. The top 4b of the hollow portion 4 is formed with a release opening 19 and an annular projection 20 extending upward and positioned along the periphery of the opening 19.

As shown in FIGS. 6 and 7, the chemical container 5 is in the form of a hollow cylinder and has a chemical agent delivery opening 16 formed in its peripheral wall 21. Engaging cavities 23, 23 for the respective pivots 15, 15 to engage in are formed in the opposed circular side walls 22, 22 of the chemical container 5 and positioned away from the center of gravity of the container 5. With the projecting pivots 15, 15 engaged in the cavities 23, 23, the chemical container 5 is made free to rotate and is in a stable state when the delivery opening is directed downward. As shown in FIG. 7, the container 5 is integrally formed on its outer periphery with a rib 5a in the form of a triangular plate for greatly displacing the center of gravity of the container 5 from the center of rotation thereof.

An annular upward projection 24 is formed on the top of the container 5 around the delivery opening 16 to provide a male screw 25.

The device has means 17 for holding the chemical container 5 against rotation and also for closing the delivery opening 16 when the container 5 is in an unstable position in which the delivery opening 16 is directed upward. The means 17 has a stopper 26 for closing the release opening 19 and the delivery opening 16. The stopper 26 has a lower portion providing a female screw 27 in engagement with the male screw 25 around the delivery opening 16. The stopper 26 is formed at its upper part with a base portion 28 having a larger diameter than the release opening 19. The base portion 28 is formed in its lower side with an annular recess 29 in which the annular projection 20 is engaged hermetically and rotatably. Consequently, the chemical container 5 containing the chemical agent 6 and positioned in the unstable posture with the delivery opening 16 directed upward is restrained from rotation about the center of the pivots 15 and has its delivery opening 16 closed with the stopper 26.

On the other hand, when the stopper 26 is rotated to release the male screw 25 from the female screw 27, the delivery opening 16 is opened and the container 5 is freed from the restraint, whereupon the chemical container 5 supported at a position away from the center of gravity thereof spontaneously rotates under gravity to direct the delivery opening 16 downward as indicated in phantom lines in FIG. 7 and place the chemical agent 6 into the waste container 2.

When the container 5 is positioned with its opening 16 directed upward, the chemical agent 6 therein will not be degraded or spill out because the container 5 is sealed off from the external environment by the stopper 26. Moreover, the delivery opening 16 can be closed and the container 5 restrained from rotation by the single stopper 26, while the opening 16 can be opened simultaneously with the release of the container 5 for rotation by manipulating the stopper 26, so that the chemical agent can be placed into the waste liquid with extreme ease. The user can handle the container 5 from outside the aspirator 1 without contacting the waste liquid 13 and the chemical agent 6. The liquid 13 can therefore be treated easily with safety.

By virtue of the construction and function described above, the waste liquid 13 containing the body fluid and filling the waste container 2 can be treated with safety upon completion of aspiration, i.e. before transport to the treating facility.

FIG. 9 is a view in section taken along the line IX—IX in FIG. 2 and showing the above-mentioned baffle plate 7 as it is seen from above. The baffle plate 7 of the present embodiment is prepared by cutting out a pair of bowlike portions from a disk which portions are symmetric with respect to the center of the disk. The interior of the waste container 2 is partitioned by the baffle plate 7 into upper and lower liquid collecting spaces 31a, 31b, which are held in communication with each other through the pair of bowlike cutouts 30, 30. To provide the baffle plate 7 in this embodiment, the waste container 2 comprises two divided portions, i.e. an upper tubular member 2a and a lower tubular member 2b. The baffle plate 7 is formed as joined to the bottom of the upper member 2a, to which the lower member 2b is welded. Thus, the tubular waste container 2 has the baffle plate 7 at an intermediate portion of its interior.

The chemical agent 6 delivered from the container 5 partly remains on the central portion 7a of the baffle plate 7 and can therefore be prevented from wholly settling on the bottom of the waste container 2. Consequently, the chemical agent 6 produces its effect also at the vertically intermediate portion of the container 2 and accordingly acts on the waste liquid 13 uniformly. This greatly shortens the time required for treating the waste liquid 13. Although the present embodiment has only one baffle plate 7, a plurality of baffle plates 7 can be provided depending on the size or the shape of the waste container 2. The baffle plate 7 need not always be formed integrally with the waste container but can be provided by being inserted into the waste container 2. The configuration of the cutouts in the baffle plate 7 can be altered suitably in conformity with the size or shape of the waste container 2.

Figure 10:
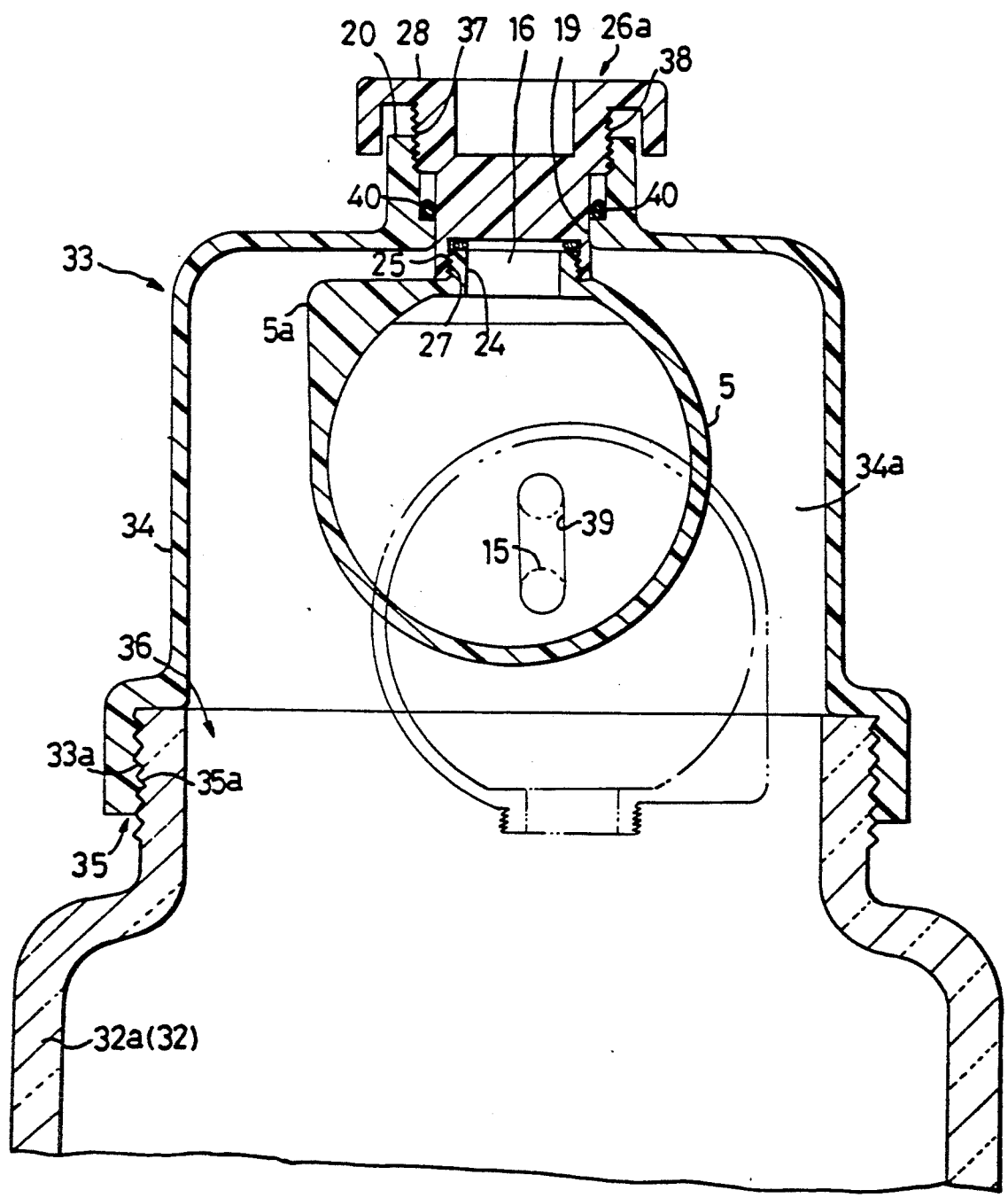
FIGS. 10 and 11 are sectional views showing another waste liquid treating device as a seventh embodiment.
Figure 11:
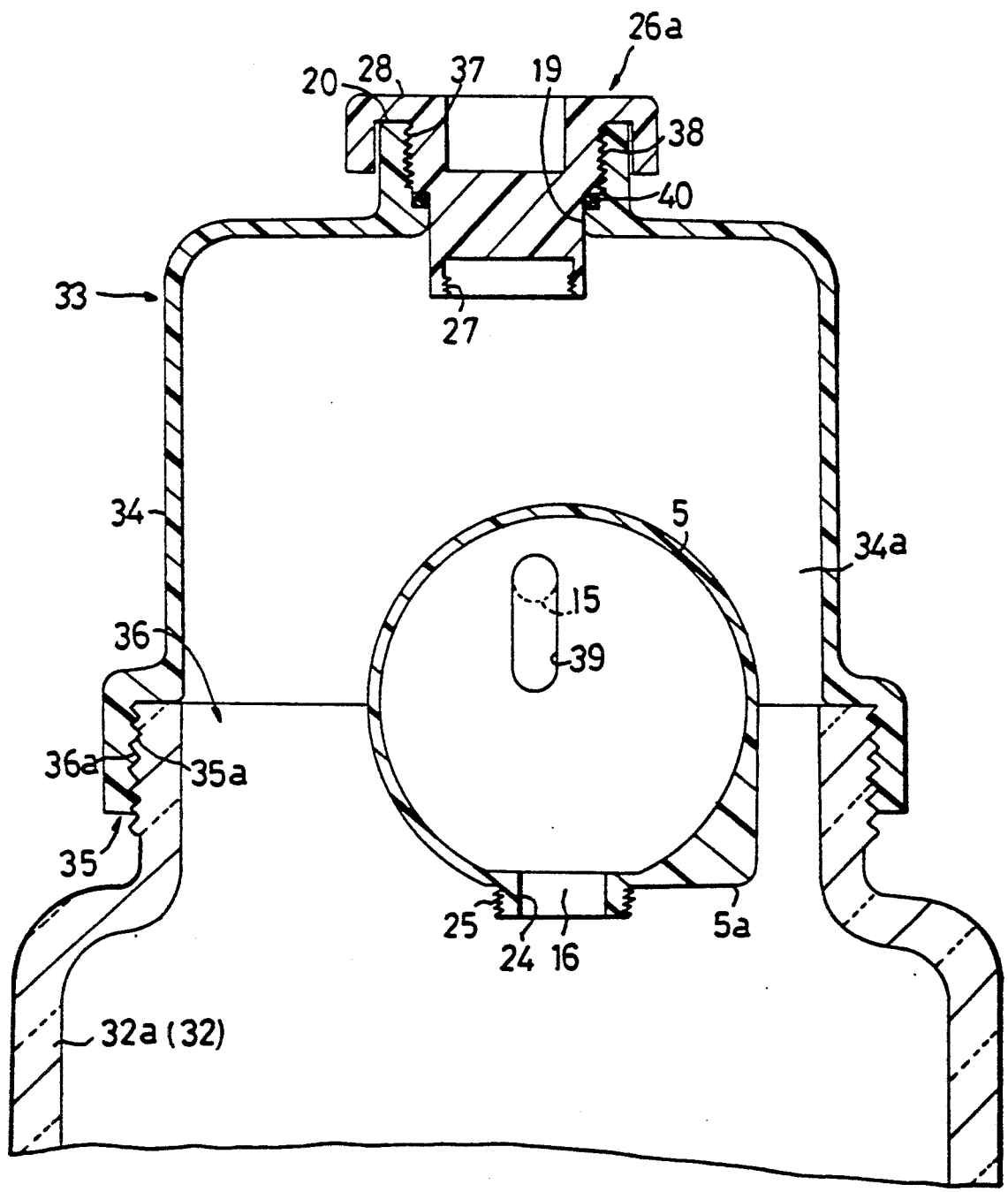

FIGS. 10 and 11 show another waste liquid treating device, i.e. seventh embodiment, wherein the invention is applied to a wide-mouthed bottle 32a which is generally used as a container 32 for collecting a waste liquid containing solids.

The waste liquid treating device 33 of the present embodiment comprises a hollow closure 34 having a socket 35 which is fittable to the top mouth 36 of the bottle 32a.

The outer periphery of the mouth 36 of the bottle 32a is threaded to provide a male screw 36a, and the socket 35 of the closure 34 is threaded to provide a female screw 35a in engagement with the male screw 36a. A chemical agent container 5 having a delivery opening 16 is rotatably supported by the closure 34 inside thereof.

More specifically, each side wall 34a of the closure 34 is formed with a projecting pivot 15 for rotatably supporting the container 5. An engaging cavity 39 for the pivot 15 to engage in is formed in each side wall of the container 5 at a position away from the center of gravity of the chemical container 5. The cavity 39 is vertically elongated and is movable upward or downward relative to the projecting pivot 15. Consequently, with each pivot 15 engaged in the cavity 39, the chemical container 5 is rotatable and movable upward or downward and is in a stable position when the delivery opening 16 is directed downward. A rib 5a in the form of a triangular plate is formed integrally on the outer periphery of the container 5 for greatly displacing the center of gravity of the container 5 from the center of rotation thereof.

The device has means for holding the chemical container 5 against rotation and also for closing the delivery opening 16 when the container 5 is in an unstable position in which the opening 16 is directed upward. This means has a stopper 26a for closing a release opening 19 formed in the top of the closure 34 and the delivery opening 16.

The stopper 26a has a lower portion providing a female screw 27 in engagement with a male screw 25 which is provided by an annular projection 24 on the container 5 around the delivery opening 16. The stopper 26a is formed at its upper part with a base portion 28 having a larger diameter than the release opening 19. The base portion 28 has a male screw 38 screwed in a female screw 37 provided by an annular projection 29 extending upward from the top of the closure 34 around the release opening 19.

According to the present embodiment, the screws 25, 27 formed around the delivery opening 16 and at the lower end of the stopper 26a, respectively, are left-handed screws (reverse screws), whereas the screws 37, 38 provided by the annular projection 20 around the release opening 19 and by the base portion 28 of the stopper 26a are right-handed screws.

With a chemical agent 6 accommodated in the container 5, the female screw 27 at the lower end of the stopper 26a is in engagement with the male screw 25 on the chemical container 5, whereby the delivery opening 16 is closed. The lower part of the male screw 38 provided by the base portion 28 of the stopper 26a is also in engagement with the female screw 37 around the release opening 19. Accordingly, the container 5 is held in an unstable position with the delivery opening 16 directed upward. In this state, the upper part of the base portion male screw 38 of the stopper 26a is positioned above the female screw 37 around the release opening 19 out of engagement with the screw 37.

When the stopper 26a of the above device is rotated clockwise from the state shown in FIG. 10, as shown in FIG. 11, the upper part of the base portion male screw 38 of the stopper 26a comes into engagement with the release opening female screw 37, while the chemical container 5 is lowered, with the result that the male screw 25 on the container 5 is brought out of engagement with the female screw 27 at the lower end of the stopper 26a, permitting the container 5 to rotate to direct the delivery opening 16 downward. Thus, the delivery opening 16 can be opened and the container 5 is freed from restraint for rotation at the same time merely by rotating the stopper 26a in one direction. The chemical agent can therefore be placed into the waste liquid with greater ease.

A seal 40 is provided between the closure 34 and the stopper 26a to completely seal the clearance between the stopper and the closure when the stopper 26a is fully fastened to the closure 34. This precludes the waste collected from spilling out from the wide-mouthed bottle 32a during transport.

The device 33 described above is attached to the wide-mouthed bottle 32a when the bottle has been filled with a waste liquid containing solids. The base portion 28 of the stopper 26a is then rotated clockwise, whereby the chemical agent is delivered from the container 5 into the waste liquid. The bottle 32a is thereafter transported to a treating facility with the device 33 attached to the bottle. Alternatively, the bottle can be transported with the device 33 removed therefrom after the treatment. The waste liquid containing solids and collected in the bottle 32a, when thus treated, is safe and reduced in the hazard of causing infection with bacteria or the like.

The waste liquid treating device 33 only can be made disposable, or both the device 33 and the waste container 32 can be made reusable.

The present invention is not limited to the foregoing embodiments. Although the embodiments described comprise a single chemical agent container, a plurality of chemical containers are usable, such that the waste liquid is first treated with an acid or like chemical agent which is hazardous to the human body and thereafter neutralized with another chemical agent.

The hollow closure 34 of the seventh embodiment may be provided at suitable portions with an outlet for communication with a suction source and an inlet for collecting a waste liquid from body cavities by suction.

What is claimed is:

1. An apparatus for coagulating body fluids which have been released from live bodies and solutions of said body fluids, said apparatus comprising:
    (a) waste a container for storing body fluids and body fluid solutions;
    (b) an aspiration port at an upper portion of said waste container for aspirating the body fluids and body fluid solutions;
    (c) a discharge port at an upper portion of said waste container;
    (d) means for holding a chemical agent in an inner upper portion of said waste container; and
    (e) a chemical agent comprising a coagulant for coagulating body fluids and body fluid solutions in said waste container.

2. A device as defined in claim 1 wherein the chemical agent holding means comprises a container for accommodating the chemical agent, and the chemical agent container communicates with the waste container through a shutoff valve.

3. A device as defined in claim 1 wherein the chemical agent holding means comprises a container for accommodating the chemical agent, and the chemical agent container communicates with the waste container through a shutoff valve, the shutoff valve serving also as a shutoff valve for a waste liquid inlet port of the waste container, the shutoff valve being operable to hold the inlet port closed while holding the chemical agent container in communication with the waste container, the shutoff valve being operable to hold the inlet port open while holding the chemical agent container out of communication with the waste container.

4. A device as defined in claim 1 wherein the chemical agent holding means comprises a container for accommodating the chemical agent, and the chemical agent container is so held as to fall inside the waste container and is permeable to aqueous solutions.

5. A device as defined in claim 1 wherein the chemical agent holding means comprises a container for accommodating the chemical agent, and the chemical agent container is so held as to fall inside the waste container and is soluble in water.

6. A device as defined claim 1 wherein the chemical agent holding means comprises a suspender for holding the chemical agent, and the suspender is held suspended within the waste container and is permeable to aqueous solutions.

7. A device as defined in claim 2 wherein the chemical agent holding means comprises a container for accommodating the chemical agent, and the chemical agent container has a chemical agent delivery opening and is so supported as to make the delivery opening changeable selectively to an upwardly directed position or to a downwardly directed position.

8. A device as defined in claim 7 wherein the chemical agent container is supported rotatably.

9. A device as defined in claim 8 wherein a center of rotation of the chemical agent container is at a position away from the center of gravity thereof so that the delivery opening is in the downwardly directed position when the chemical agent container is in a stable state, the device further having means for releasably holding the chemical agent container in a position in which the delivery opening is directed upward.

10. A device as defined in claim 9, wherein the chemical agent container is made movable from outside the waste container to change the delivery opening from the upwardly directed position to the downwardly directed position.

11. A device as defined in claim 9 wherein the means for releasably holding the chemical agent container serves also as means for openably closing the delivery opening.

12. A device as claimed in claim 11, wherein the chemical agent container is made movable from outside the waste container to change the delivery opening from the upwardly directed position to the downwardly directed position.

13. A device as defined in claim 8, wherein the chemical agent container is made movable from outside the waste container to change the delivery opening from the upwardly directed position to the downwardly directed position.

14. A device as defined in claim 7 wherein the chemical agent container is made movable from outside the waste container to change the delivery opening from the upwardly directed position to the downwardly directed position.

15. A device as defined in claim 14 wherein the chemical agent holding means comprises a hollow closure for closing an upper opening of the waste container, the hollow closure being formed with a release opening located above the delivery opening as directed upward, the release opening being closed with a stopper for closing the delivery opening.

16. A device as defined in claim 15 wherein the stopper is in screw-thread engagement with respective threaded portions of the delivery opening and the release opening, and the threaded portions are in oppositehanded screw relationship with each other, the chemical agent container being so supported as to be movable upward or downward relative to the hollow closure.

* * * * *